United States Patent [19]

Grant

[11] Patent Number: 4,947,869
[45] Date of Patent: Aug. 14, 1990

[54] PATIENT RESTRAINT DEVICE

[76] Inventor: Oliver J. Grant, 7312 S. Scherrei Dr., Franklin, Wis. 53132

[21] Appl. No.: 468,202

[22] Filed: Jan. 22, 1990

[51] Int. Cl.⁵ ............................................. A61F 13/00
[52] U.S. Cl. .................................... 128/874; 128/869; 128/873; 119/96
[58] Field of Search .................. 119/96, 106; 128/869, 128/873, 874

[56] References Cited

U.S. PATENT DOCUMENTS

| | | | |
|---|---|---|---|
| D. 275,230 | 8/1984 | Hubbard et al. | 128/874 X |
| 1,923,001 | 8/1933 | Haga | 128/874 |
| 3,137,294 | 6/1964 | Robertson | 128/874 |
| 3,181,530 | 5/1965 | Storey | 128/874 |
| 3,276,432 | 10/1966 | Murcott | 119/96 |
| 4,840,189 | 6/1989 | Wachtel | 128/869 |

*Primary Examiner*—Robert A. Hafer
*Assistant Examiner*—Beth Anne Cicconi
*Attorney, Agent, or Firm*—Fuller, Ryan & Hohenfeldt

[57] ABSTRACT

A patient restraint device for restraining invalid patients and the like. A generally unitary vest body has two face portions merging at the shoulder, and a neck opening formed between the shoulders. Each of the face portions has a distal edge formed at the ends of the faces furthest removed from the neck opening. Each of the faces terminates at the distal edge portion in straps. Two such straps are provided for each of the faces, one at each side edge thereof. The distal edge of one of the faces is longer than the distal edge of the other of the faces. An opening is formed in the face having the longer of the two distal edges, and adapted to receive at least two of the straps. The opening is a single vertical slot positioned just above and at the center of the distal edge of the face having the longer distal edge. The method for using the device includes sliding the neck opening over the head of the patient, and orienting the device front to back so as to give the patient the desired amount of restraint and freedom. Then the bottom edges are wrapped about the patient and the straps from the face portion with the shorter sides are threaded into the opening. All of the straps are then secured to suitable nearby supports.

7 Claims, 2 Drawing Sheets

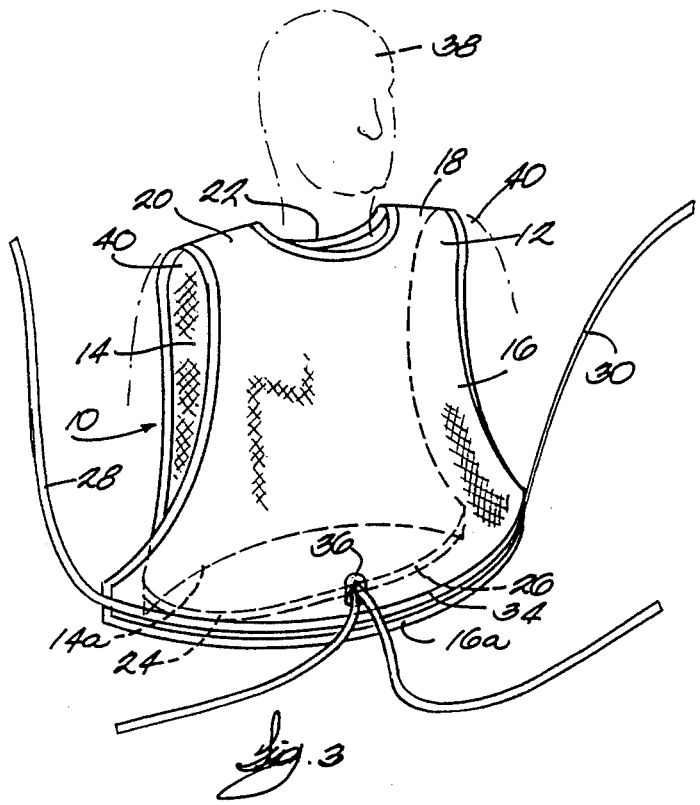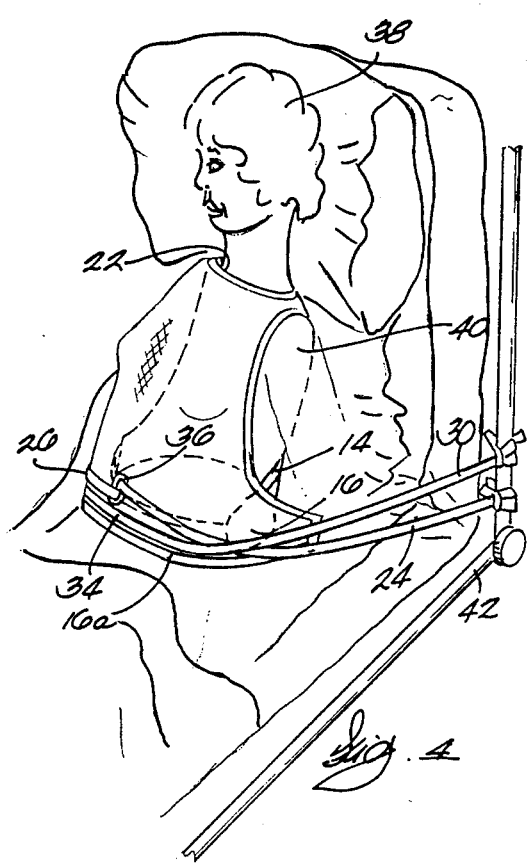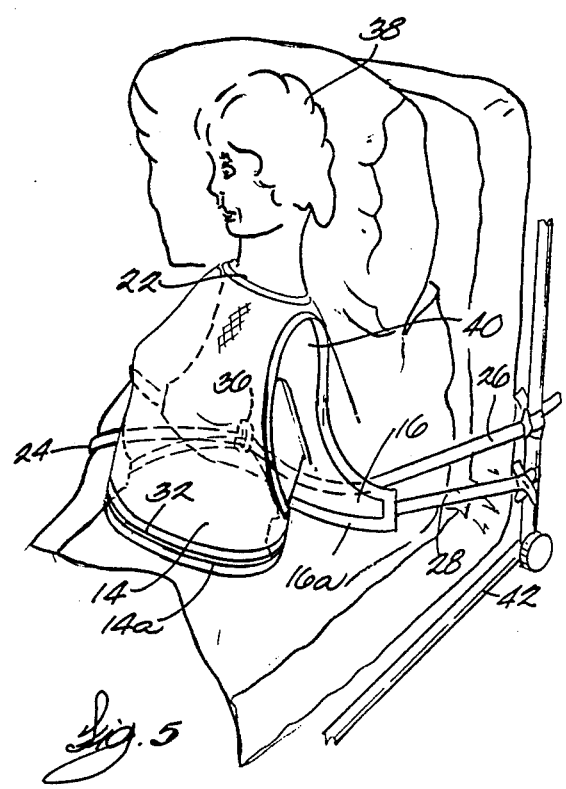

PATENT RESTRAINT DEVICE

BACKGROUND OF THE INVENTION

This invention relates to patient restraint devices, and particularly to vest-type restraint devices directed toward invalid patients, who need and can be afforded varying amounts of freedom of movement.

It is well known to provide vest-type restraint devices to restrain patients who are likely to fall out of bed and cause harm to themselves thereby. Examples of such restraint devices are disclosed in numerous patents, such as Storey, U.S. Pat. No. 3,181,530, and Hubbard, et al, U.S. Pat. No. Des. 275,230. As can be seen from FIGS. 4, 6 and 7 of the Storey patent, however, one problem which has existed with some of these restraints is that bunching of material and straps may occur, which could cause substantial discomfort and even bedsores and other ailments in chronically bedridden patients. The Hubbard, et al, patent may be an attempt to solve the bunching problem by use of a vest that is in two parts. However, this two-piece construction adds a level of expense and complexity of use that may be unacceptable to certain patients and caretakers. What is needed is a vest-type restraint device that is both easy to use and unlikely to irritate the patient's skin or cause other ailments.

This invention relates to improvements to the apparatus described above and to solutions to the problems raised or not solved thereby.

SUMMARY OF THE INVENTION

This invention relates to a patient restraint device for restraining invalid patients and the like. The invention includes a generally unitary vest body having two face portions merging at the shoulder, and having a neck opening formed between the shoulders. Each of the face portions has a distal edge formed at the ends of the faces furthest removed from the neck opening. Each of the faces terminates at the distal edge portion in straps. Two such straps are provided for each of the faces, one at each side edge thereof. The distal edge of one of the faces is longer than the distal edge of the other of the faces. An opening is formed in the face having the longer of the two distal edges, and adapted to receive at least two of the straps. The opening is a single vertical slot positioned just above and at the center of the distal edge of the face having the longer distal edge.

The invention also includes a method of restraining a patient, such as an invalid patient or the like. This method includes providing a restraint vest which substantially includes the elements indicated above. According to the method, the neck opening is slid over the head of the patient, and oriented front to back so as to give the patient the desired amount of restraint and freedom. Then the bottom edges are wrapped about the patient so as to tightly secure the vest to the patient, and the straps from the face portion with the shorter sides are inserted into the opening. All of the straps are then secured to suitable convenient support or securement means.

Other objects and advantages of the invention will become apparent hereinafter.

DESCRIPTION OF THE DRAWING

FIG. 3 is a view of the vest shown in FIG. 1 from a frontal angle showing some of the straps threaded through the slot in the larger face and wrapped about the patient.

FIG. 4 is an isometric view of the vest shown in FIG. 1 applied to a patient in bed so as to afford a lesser level of freedom of movement.

FIG. 5 is an isometric view of the vest shown in FIG. 1 applied to a patient in bed so as to afford a greater level of freedom of movement.

DESCRIPTION OF THE PREFERRED EMBODIMENT

Figure 1:
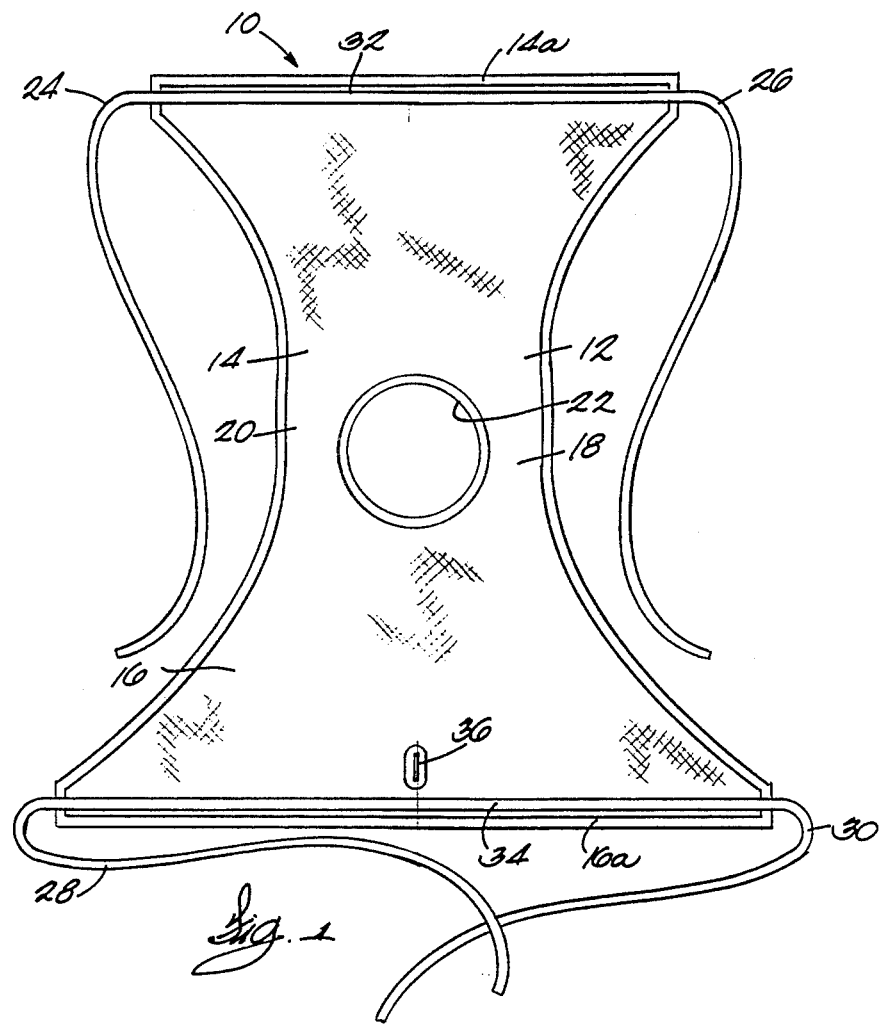
FIG. 1 is a top plan view of a restraint vest constructed substantially according to one embodiment of the invention, laid out substantially flat.

Referring now to FIG. 1, there is shown a patient restraint device 10 constructed according to a preferred embodiment of the present invention. The device 10 is provided more as a support device than as a restraint device, providing varying levels of support or restraint according to the needs of the patient to which it is applied. As such it is generally intended to be applied to invalid or elderly patients.

As shown in FIG. 1, the device 10 has a vest body 12 of generally unitary construction. The vest body 12 includes two face portions 14 and 16 merging at shoulder portions 18 and 20, and having a neck opening 22 formed between the shoulder portions. Each of the face portions 14 and 16 has a distal edge portion 14a and 16a respectively formed at the ends of the face portions furthest removed from the neck opening 22. One of the distal edge portions, edge portion 14a of the face portion 14, is shorter than the other edge portion 16a. Preferably the shorter edge portion 14a is about 65 to 80 percent of the length of the longer edge portion 16a, and most preferably the shorter edge portion is two-thirds to three-fourths of the length of the longer edge portion. Each of the respective distal edge portions, however, is substantially longer than the combined width of the neck opening 22 and shoulder portions 18 and 20. Each of the face portions 14 and 16 has side edge portions which preferably curve smoothly outward from the shoulder portions 18 and 20 to the respective distal edge 14 or 16.

The face portion 14 has a pair of side straps 24 and 26, one attached to each side edge of the face portion at the distal edge 14a. Correspondingly, the face portion 16 has a pair of side straps 28 and 30, one attached to each side edge of the face portion at the distal edge 16a. In the most preferred embodiment, each pair of straps, 24 and 26 on face portion 14 and 28 and 30 on face portion 16, are formed of a single piece of strapping for improved strength and support. That is, straps 24 and 26 are formed of a single strap 32, attached along the entire distal edge 14a of the face portion 14, and straps 28 and 30 are formed of a single strap 34, attached along the entire distal edge 16a face portion 16.

The invention further calls for an opening 36 formed in the face portion 16 having the longer distal edge portion 16a. The opening 36 is adapted to receive the two straps 24 and 26 from the face portion 14 having the shorter distal edge portion 14a. As shown in the figures, the opening 36 is most preferably a single vertically oriented slot positioned just above and at the center of the longer distal edge 16a.

Figure 2:
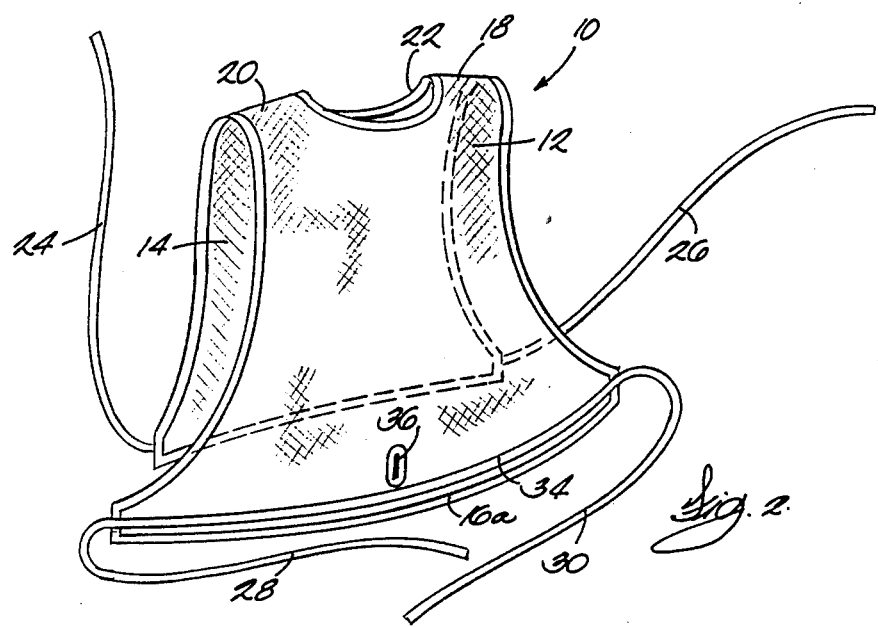
FIG. 2 is a view of the vest shown in FIG. 1 from a frontal angle showing the straps and faces of the vest ready to be wrapped about the patient.

In use, then, the device 10 is generally considered in the upright position as shown in FIG. 2. As shown in FIG. 3, the neck opening 22 of the device 10 is first slid over the head of the patient 38, and the shoulder portions 18 and 20 set to rest on the shoulders 40 of the patient. The device 10 is then oriented front to back, so as to give the patient 38 the desired amount of restraint and freedom. That is, if greater restraint and support is desired, device 10 is oriented so that the shorter face 14 is at the back and the longer face 16 at the front, as generally shown in FIG. 4. Alternatively, if greater freedom of movement is desired to be provided to the patient 38, the device 10 is oriented the other way, that is, with the longer face 16 at the back and the shorter face 14 at the front.

The straps from the face portion 14, with the shorter distal edge 14a, are then threaded into the opening 36, as shown in FIG. 3. The distal edge portions 14a and 16a may then be wrapped about the patient 38 so as to tightly secure the device 10 to the patient. Finally, all of the straps are secured to suitable convenient support means, such as bed frame members 42, FIGS. 4 and 5.

Hence this invention provides a patient restraint and support device 10, providing varying levels of support or restraint according to the needs of the patient to which it is applied.

While the device hereinbefore described is effectively adapted to fulfill the aforesaid objects, it is to be understood that the invention is not intended to be limited to the specific preferred embodiment of patient restraint device set forth above. Rather, it is to be taken as including all reasonable equivalents within the scope of the following claims.

I claim:

1. A patient restraint device for restraining invalid patients and the like, comprising:
    a generally unitary vest body having two face portions merging at shoulder portions, and having a neck opening formed between said shoulder portions;
    each of said face portions having a distal edge portion formed at the ends of said face portions furthest removed from said neck opening;
    each of said face portions terminating at said distal edge portion in horizontal straps, two such straps for each of said face portions, one at each side edge thereof;
    said distal edge portion of one of said face portions being longer than said distal edge portion of the other of said face portions; and
    an opening formed in said face portion having the longer of the two distal edge portions, adapted to receive said two straps from said face portion having the shorter of the two distal edge portions.

2. A patient restraint device as recited in claim 1 wherein said opening is a slot positioned just above said distal edge of said face portion having the longer distal edge.

3. A patient restraint device as recited in claim 1 wherein said opening is a single vertical slot positioned just above and at the center of said distal edge of said face portion having the longer distal edge.

4. A patient restraint device as recited in claim 1 wherein the length of said distal edge of each of said face portions is substantially longer than the combined width of said neck opening and shoulder portions.

5. A patient restraint device as recited in claim 4 wherein each of said face portions has side edge portions which curve smoothly outward from the shoulder portions to said distal edge.

6. A method of restraining a patient, such as an invalid patient or the like, comprising:
    A. providing a restraint vest which includes:
        (1) a generally unitary vest body having two face portions merging at shoulder portions, and having a neck opening formed between said shoulder portions,
        (2) each of said face portions having a distal edge portion formed at the ends of said face portions furthest removed from said neck opening,
        (3) each of said face portions terminating at said distal edge portion in horizontal straps, two such straps for each of said face portions, one at each side edge thereof,
        (4) said distal edge portion of one of said face portions being longer than said distal edge portion of the other of said face portions, and
        (5) an opening formed in said face portion having the longer of the two distal edge portions, adapted to receive said two straps from the face portion having the shorter of the two horizontal portions;
    B. sliding said neck opening over the head of the patient, and orienting the restraint vest front to back, so as to give the patient the desired amount of restraint and freedom;
    C. inserting the straps from the face portion with the shorter sides into said opening; and
    D. securing all of said straps to suitable convenient support means.

7. A method as recited in claim 6 further comprising, after the inserting step, wrapping said distal edge portions about the patient so as to tightly secure said vest to said patient.

* * * * *

UNITED STATES PATENT AND TRADEMARK OFFICE
CERTIFICATE OF CORRECTION

PATENT NO. : 4,947,869
DATED : August 14, 1990
INVENTOR(S) : OLIVE J. GRANT

It is certified that error appears in the above—identified patent and that said Letters Patent is hereby corrected as shown below:

On the face of the patent at [76],

DELETE   "Oliver J. Grant"

SUBSTITUTE   --- OLIVE J. GRANT ---

Signed and Sealed this

Seventh Day of January, 1992

Attest:

HARRY F. MANBECK, JR.

*Attesting Officer*      *Commissioner of Patents and Trademarks*